(12) United States Patent
Dye

(10) Patent No.: US 6,875,237 B2
(45) Date of Patent: *Apr. 5, 2005

(54) DRIVING INSTRUMENT WITH VARIABLY ANGLED JOINT AND EXTENDED TIP AND METHOD OF USE FOR MINIMALLY INVASIVE HIP SURGERY

(75) Inventor: Donald Dye, Pflugerville, TX (US)

(73) Assignee: Zimmer Austin, Inc., Austin, TX (US)

( * ) Notice: Subject to any disclaimer, the term of this patent is extended or adjusted under 35 U.S.C. 154(b) by 136 days.

This patent is subject to a terminal disclaimer.

(21) Appl. No.: 10/375,455

(22) Filed: Feb. 27, 2003

(65) Prior Publication Data
US 2004/0172039 A1 Sep. 2, 2004

(51) Int. Cl.[7] .................................................. A61F 2/32
(52) U.S. Cl. .................................................. 623/22.21
(58) Field of Search ........................... 623/22.21, 22.12, 623/22.24, 22.25, 22.28; 606/91, 99, 81, 80, 180; 128/898

(56) References Cited

U.S. PATENT DOCUMENTS

| | | | | |
|---|---|---|---|---|
| 4,305,394 A | * | 12/1981 | Bertuch, Jr. | 606/91 |
| 5,037,424 A | * | 8/1991 | Aboczsky | 606/91 |
| 5,584,837 A | * | 12/1996 | Petersen | 606/91 |
| 5,683,399 A | * | 11/1997 | Jones | 606/91 |
| 5,904,689 A | * | 5/1999 | Jonjic | 606/99 |
| 6,695,850 B2 | * | 2/2004 | Diaz | 606/91 |

* cited by examiner

Primary Examiner—Pedro Philogene
(74) Attorney, Agent, or Firm—Jonathan D. Feuchtwang

(57) ABSTRACT

A method and apparatus for performing minimally invasive hip surgery for implanting a prosthetic acetabular component into a natural acetabulum. The method and apparatus include a driving instrument and driving guide for aligning and driving bone screws and screw-hole plugs. The instrument includes a working section and a driving section connected together with a joint connector. The joint connector enables the working and driving sections to move to various angles relative to each other.

20 Claims, 3 Drawing Sheets

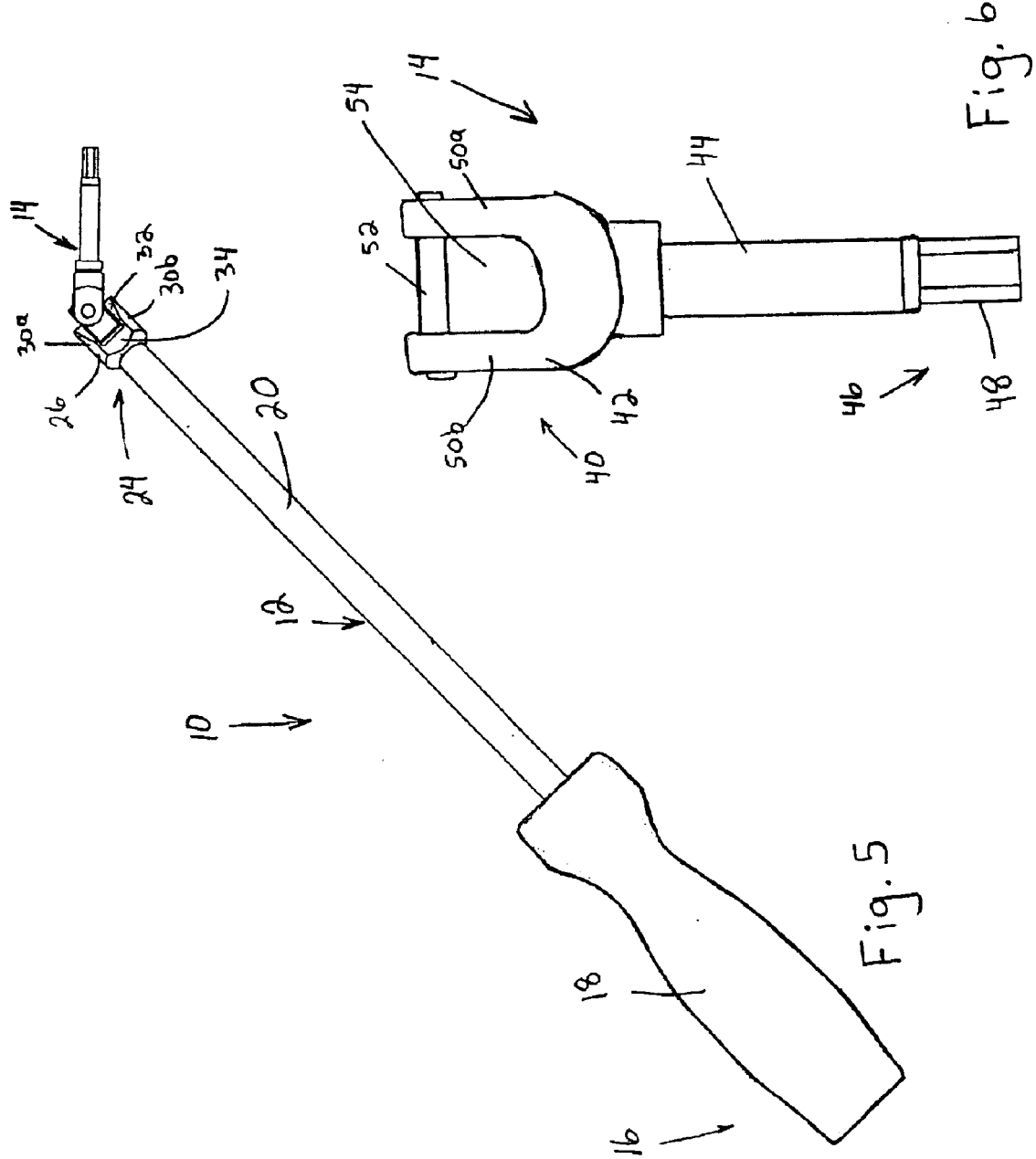

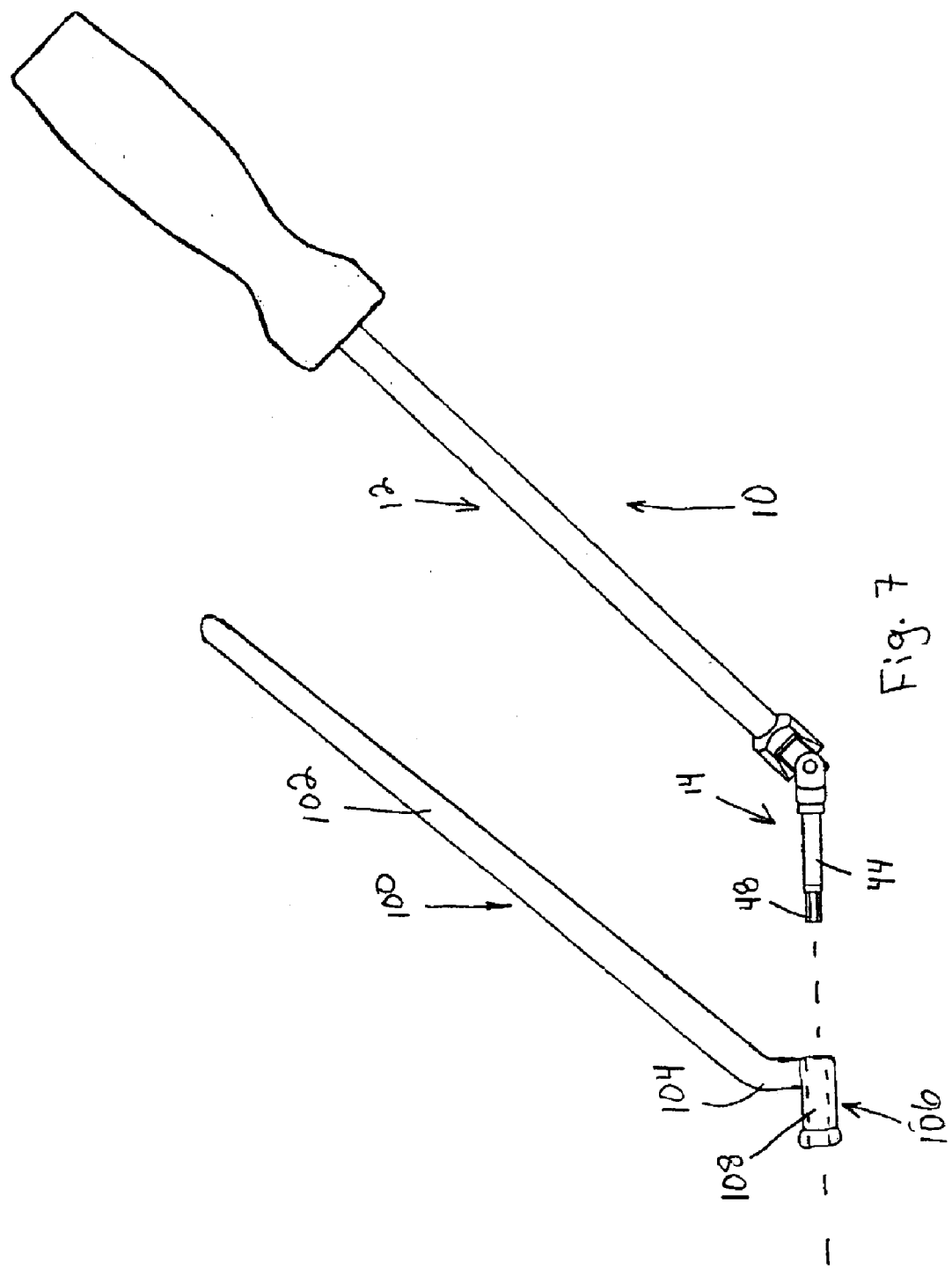

DRIVING INSTRUMENT WITH VARIABLY ANGLED JOINT AND EXTENDED TIP AND METHOD OF USE FOR MINIMALLY INVASIVE HIP SURGERY

FIELD OF THE INVENTION

The disclosure herein generally relates to a method and apparatus for performing minimally invasive hip replacement surgery for the acetabulum using a driving instrument with a variably angled joint and extended tip.

BACKGROUND OF THE INVENTION

Traditional hip replacement surgery has been used in the United States since as early as the 1960's. The surgical technique to implant a hip has not drastically changed over the years, and today, this technique is quite successful. In fact, the surgical technique is prolifically used throughout the world and has a known success rate of over 90%. Certainly, the traditional surgical technique is fundamentally sound and predictable.

Unfortunately, traditional techniques to implant a hip have well recognized shortcomings. Most importantly, a rather large incision is made on the side of the hip. The incision can extend from 6 to 12 inches; the actual length of the incision depends on the size of the patient and type of surgery (revision versus total hip arthroplasty, for example). A long, deep incision can divide a number of important stabilizing muscles and tendons and further damage the hip joint and surrounding soft tissue. Inevitably, long incisions lead to larger blood losses, longer rehabilitation times for patients, and unsightly scar lines. A patient can easily spend four or five days in the hospital after a total hip arthroplasty, for example.

Recently, surgeons have been developing new, less invasive surgical techniques to perform total hip arthroplasty and revision hip surgery. Minimally invasive surgery, or MIS, is one such technique with great promise to become a popular and accepted technique for implanting a hip.

MIS has significant advantages over traditional hip replacement surgery. Most importantly, a rather small incision is made on the side on the hip. This incision is approximately 3 to 5 inches long, and the benefits of a shorter incision are enormous.

First and foremost, the patient can recover in a much shorter period of time after a MIS. The recuperation time in the hospital can be a few days and significantly reduce the cost to both the patient and hospital. In fact, some patients are leaving the hospital within 24 to 48 hours after the surgery. Obviously, this shortened time period is extremely important to the patient.

As another advantage, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Presently, instruments to perform MIS are being developed and refined. These instruments have a vital role in the ability to perform a successful minimally invasive surgery. These instruments, for example, must enable the surgeon to place the hip implant in a very precise location. If the implant is not accurately placed, then complications, such as dislocation or subluxation, can occur. Further and most importantly, the instruments must consistently and reliably perform through a small three inch opening in the patient.

A successful design of instruments for MIS has other challenges as well. Specifically, the instrument must be easy to use and facilitate the implantation procedure. If the MIS instrumentation is too cumbersome or not easy to manipulate, then the surgeon will be less likely to use minimally invasive surgery. The patient, then, will not reap the benefits MIS has to offer.

As yet another consideration, MIS instrumentation must appeal to a wide range of orthopedic surgeons with various skills and experience. If, for example, the instruments are too complex and complicated, then they will not be appealing and accepted in the orthopedic surgical community. Further yet, the training and skill level required to use the instruments and become proficient with them, cannot be overly taxing on the orthopedic surgeons.

While implanting or repairing a prosthetic acetabular shell in MIS for instance, screw-hole plugs and dome plugs must be screwed in the acetabular shell. Further, bone screws must be driven through screw-holes in the acetabular shell and into surrounding cortical bone to secure the shell to this bone. Traditional surgical driving instruments, though, are not shaped and sized to engage a screw-hole plug or bone screw and place it through the acetabular shell. For one reason, the screw-hole openings in the acetabular shell are at an angle with respect to the surgical site. Thus, a straight driving instrument will not have the proper angulation to reach the screw-hole opening in the shell.

Great care must be taken while placing a screw-hole plug or dome plug in the acetabular shell. If the threads on the plug do not properly align with the threads in the shell, then these threads can become stripped or cross-threaded. In such instances, the acetabular shell may have to be removed and replaced during the surgical procedure. Further yet, great care must be taken while placing a bone screw through the screw-hole opening in the acetabular shell. If the bone screw is not placed with the correct angle, then the bone screw may not seat well in the screw-hole opening. Additionally, the bone screw may not properly engage cortical bone to hold the shell in place in the acetabulum.

In short, instruments, and in particular driving instruments for screw-hole plugs and bone screws, play a vital role in MIS surgery for hip implantation. It therefore would be advantageous to provide a new method and accompanying instruments for driving and aligning screw-hole plugs and bone screws in minimally invasive surgery to implant a prosthetic hip.

SUMMARY OF THE INVENTION

The present invention is directed to a method and apparatus for performing minimally invasive hip replacement surgery for the acetabulum using a driving instrument with a variably angled joint connector and extended tip. The driving instrument is adapted to drive screw-hole plugs and bone screws at an angle into a prosthetic acetabular shell. The driving instrument also includes a driving guide adapted to guide the instrument while driving the screw-hole plugs and bone screws.

The method of the present invention generally comprises the steps of templating the acetabulum to estimate the size of reamer and acetabular components; incising the surgical site with a single incision approximately three to five inches in length; retracting soft tissue at the surgical site; dislocating the hip from the acetabulum; reaming the acetabulum with a reamer; inserting and aligning a trial shell into the reamed acetabulum; inserting and aligning a trial insert to the trial shell; removing the trial insert and shell; inserting and aligning an implant shell into the reamed acetabulum; impacting the implant shell with a acetabular shell impaction instrument; providing a driving instrument having a working section and a driving section with the two sections connected with a variably angled joint connector; connecting a screw-hole plug to the driving section of the driving instrument; aligning and inserting the screw-hole plug into the implant shell; connecting a bone screw to the driving section of the driving instrument; aligning and inserting the bone screw into the implant shell; inserting and impacting an implant insert into the implant shell; and closing the surgical site.

One important advantage of the present invention is that the method and driving instrument are used in a minimally invasive orthopedic hip surgery. A single, small three to five inch incision is made at the surgical site on the side on the hip. The method of the present invention, thus, enjoys the benefits of a shorter incision compared to traditional hip surgery that uses a much longer incision. As one benefit, the patient can recover in a much shorter period of time after a MIS. The recuperation time in the hospital can be a few days and significantly reduce the cost to both the patient and hospital. This shortened time period is extremely important to the patient. Further, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Another important advantage of the present invention is that the driving instrument uses a variably angled joint connector. The driving instrument can drive a screw-hole plug or bone screw while the working section and driving section are at various angles to each other. The various angles between the working and driving sections and the size and shape of the driving instrument are specifically designed and adapted to be used in minimally invasive surgical techniques for aligning and driving screw-hole plugs and bone screws into a prosthetic acetabular shell.

Another important advantage of the present invention is that the various angulations of the driving section of the driving instrument keep the handle away from the entrance to the surgical site. In MIS, it is particularly important to maintain a clear and unobstructed access to the surgical site since it is so small, measuring approximately 3–5 inches in length. Further, it is important not to disrupt or aggravate the sides of the wound channel during the surgical procedure. In the present invention, the handle and working section extend outwardly and away from the sides of the surgical site. The instrument, thus, can be used without unnecessarily disrupting or aggravating the surgical site.

As a further advantage, the handle and working section can be easily maneuvered through various angles around the surgical site while the driving section drives a screw-hole plug or bone screw into the acetabular shell. The surgeon can manipulate or move the handle to obtain a desired angle for driving the screw-hole plugs and bone screws. The handle, for example, can be moved to provide a better angle for driving the plug and screw or moved to provide a better angle for observing into the surgical site.

The driving instrument generally comprises a body having two primary sections, a working section and a driving section. The working section includes a handle at a proximal end and an elongated shaft connected to a working head portion at a distal end. The driving section has a driving head at a proximal end, a drive shaft extending from the head, and a driving tip at a distal end. This driving tip is shaped and sized to engage a screw-hole plug or bone screw and carry this plug or screw to the acetabular shell embedded in the natural acetabulum. The screw or plug can then be driven into the acetabular shell with the driving instrument. A joint connector connects the working head of the working section to the driving head of the driving section. This joint enables the working section to rotate the driving section while the two sections are disposed at an angle with respect to each other. Preferably, the joint connector is U-joint connector that offers variable angulations between the working section and driving section. A driving guide may be attached to the driving tip of the driving section. The driving guide helps align and guide the driving instrument while a screw-hole plug or bone screw is inserted into the acetabular shell. The driving instrument is discussed in more detail with reference to the figures.

As another advantage, the driving instrument can consistently and reliably perform through a small three to five inch opening in the patient. Importantly, the driving section has an extended driving shaft. The length of this driving shaft is specifically sized to reach the acetabular shell while it is embedded in the natural acetabulum.

Further yet, the instrument is easy to use and facilitates the implantation procedure. As such, the driving instrument can appeal to a wide range of orthopedic surgeons with various skills and experience. Further yet, the training and skill level required to use the instrument and become proficient with it is not overly taxing on the orthopedic surgeon.

BRIEF DESCRIPTION OF THE DRAWINGS

FIG. 5 is a side view of the driving instrument of the present invention.

FIG. 6 is an enlarged view of the driving section of the driving instrument.

FIG. 7 is an exploded side view of driving guide connecting to the driving instrument.

DETAILED DESCRIPTION

The instruments, method, and steps of the present invention are now described in more detail. The method describes the steps to perform a minimally invasive surgery to implant a prosthetic acetabular component into the natural acetabulum of a patient. Some of these steps described in the method are known to those skilled in the art and will not be discussed in great detail. Further, one skilled in the art will appreciate that certain steps may be altered or omitted while other steps may be added without departing from the scope of the invention. The novel steps of the present invention, for example, can be applied to total hip arthroplasty, to revision surgeries for total and partial hip replacement, and to other orthopedic hip surgeries using minimally invasive surgical techniques.

To facilitate a discussion of the present invention, the method of implanting a prosthetic acetabular component is divided into a plurality of steps or sections. Each of these sections is discussed seriatim.

More specifically, the method of the present invention teaches how to implant a prosthetic acetabular shell and insert into the natural acetabulum using a driving instrument with a variably angled joint connector and an extended driving section. For illustrative purposes, the discussion focuses on implanting a Converge™ Acetabular System of Centerpulse Orthopedics Inc. of Austin, Tex. This system illustrates one possible acetabular system that can be used. One skilled in the art will appreciate that other, different acetabular systems can also be used with the method and apparatus of the present invention without departing from the scope of the invention.

Templating the Acetabulum

Typically, the side of the acetabulum to be reconstructed is templated. Use of a template enables the surgeon to make an estimation of the size of reamers to be used and the size of acetabular component to be inserted. The acetabulum is templated on the both the anterior-posterior (A/P) and lateral radiographs. The hemisphere of the acetabular component is aligned with the mouth of the bony, natural acetabulum while simultaneously avoiding any osteophytes. On the A/P radiograph, the acetabular component should rest on the floor of the cotyloid notch and may touch the illoishial line. Further, the component should have a maximum lateral opening of about 40°. On the groin lateral radiograph, the cup size selected should contact the anterior and posterior rim of the bony, natural acetabulum and the medial subchondral bone. A correct position of the acetabular component will anatomically reproduce the center of rotation of the femoral head. If a bony defect is identified, use the correctly placed template to measure for proper size of the acetabular component and determine any need for bone graft.

Figure 1:
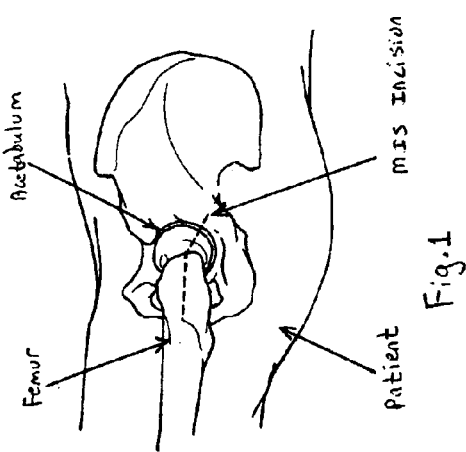
FIG. 1 is a view of a patient showing a femur and femoral head positioned in the acetabulum with an MIS incision marked along the hip.

Incising the Surgical Site (see FIG. 1)

A relatively small, single minimally invasive incision is made at the surgical site. A minimally invasive incision for this procedure has a length from about 2½ inches to about 4 or 5 inches. The incision is slightly curved or straight, commences near the vastus tubercle, and continues toward the greater trochanter and posterior inferior spine. The incision should be carried down through subcutaneous tissue and fascia lata. Any muscle tissue should be gently split in line with its fibers. At this time, a leg length measurement can be taken using techniques known in the art.

Providing Retractors

The retractors have an elongated, flat, thin body with two primary sections, a handle section and a retracting section. The handle section is elongated and adapted to be gripped with a hand. A smooth curved section transitions the handle section to the retracting section. The retracting section has a paddle with a prong that curves outwardly and away from the paddle and handle section.

Exposing the Acetabular Joint & Dislocating the Hip from the Acetabulum

Next, the knee is flexed, and the leg is internally rotated. Using a hot knife, the piriformis, short external rotators, quadratus femoris, and some posterior capsule are incised off the posterior trochanter to expose the lesser trochanter. Dislocation of the hip can now occur. A bone hook or skid may be used to avoid excess torsion on the femoral shaft.

At this time, retractors may be placed, for example under the femoral head or lesser trochanter, in order to achieve visualization for proper transection of the femoral neck if this procedure is desired at this time. If such transection occurs, the femoral neck should be transected at the templated level. Then retract the femur in an anterior direction to expose the acetabulum. Care should be taken to protect the sciatic nerve.

The retractor can be placed on the pelvis to hold the femur in an anterior position to the acetabulum. The capsule can be retracted in the posterior using retractors or pins. After the labrum and osteophytes are removed, at least a partial view of the acetabulum should be available.

Providing an Acetabular Reamer

An acetabular reamer is provided to ream the natural acetabulum. The reamer is designed and adapted to be used with minimally invasive surgical techniques of the acetabulum. Specifically, the reamer is shaped to fit through the small incision at the surgical site. Further, the reamer is angled so the distal end properly engages the natural acetabulum with the correct angular orientation and without disrupting the incision and surrounding soft tissue.

Reaming the Acetabulum

Reaming of the acetabulum should begin with a reamer that is two sizes smaller than the preoperatively selected acetabular component size. A smaller reamer ensures that the fit does not exceed the anterior-posterior diameter. Of course, the reamer should not be so small that excessive anterior or posterior reaming occurs.

After an appropriately sized reamer is connected to the acetabular reamer, reaming should begin transversely toward the cotyloid notch. The ridges of the horseshoe (or medial osteophytes) should be removed. Reaming then continues in the position of desired anteversion while simultaneously creating a hemisphere. Larger reamers are used until the anterior and posterior rim of the acetabulum is contacted. The reamer should not be sunk below the superior rim of the bony acetabulum or reamed through the cortical bone of the cotyloid notch. Cancellous bone will be evident where the horseshoe ridges have been removed. The proper size trial shell should be selected according to the size of the reamer.

Providing an Acetabular Shell Impaction Instrument

An acetabular shell impaction instrument is provided to align and then impact the acetabular shell into the natural acetabulum. The instrument is designed and adapted to be used with minimally invasive surgical techniques of the acetabulum. Specifically, the instrument has a curved shape to fit through the small incision at the surgical site and precisely impact the implanted shell at the correct angular orientation. Further, this curvature enables the instrument to engage the shell in the acetabulum without disrupting the incision and surrounding soft tissue. Further yet, the instrument is adapted to move and align the acetabular shell while it is positioned in the acetabulum. It is important to position properly the shell before it is impacted and permanently seated in the acetabulum.

Inserting a Trial Shell into the Acetabulum

The acetabular shell impaction instrument keys off the dome of the trial shell and is threaded or engaged in place.

The instrument may offer anteversion and abduction references and rotational control. Preferably, the distal end of the instrument is adapted to mate with both the trial shell and implant shell in one single orientation. To connect the components, the distal end of the instrument is keyed and threadably attached to the trial shell. One skilled in the art will appreciate that the instrument, inserts, and shells can connect in various ways.

After the trial shell is inserted into the acetabulum, its position is verified through a trial window. The edge of the trial shell should be level with the anterior-inferior margins of the acetabulum and should completely fill the anterior-posterior bony acetabulum. The instrument can be used to move and align shell while it is positioned in the acetabulum. At this time, the trial shell can be manually tested to ensure that it is stable. If the trial is loose, then use the next larger size. If the trial is too tight, then ream the rim of the acetabulum. Importantly, the trial shell should be stable before selecting a similarly sized acetabular implant shell.

Inserting a Trial Insert into the Trial Shell

Now, the trial insert is ready to be placed in the trial shell. An instrument is engaged in the rim of the trial insert and it is positioned inside the cavity of the trial shell. The trial insert contains a captured screw at the apex and can be threaded into the dome of the trial shell with the driving instrument and driving guide of the present invention. The trial components should be checked for proper fit and size.

At this point, the trials are removed from the surgical site. One skilled in the art, though, will appreciate that the trials could be temporarily left inserted to the natural acetabulum to articulate with a trial femoral prosthesis in a total hip replacement surgery.

Inserting an Implant Shell into the Acetabulum

Some implant shells may be provided with flared rims and outer bone engaging spikes. In order to insert such a shell, cancellous bone slurry may be added within the acetabulum to fill existing bone cysts and provide an interface layer. Addition of this slurry typically occurs in total hip arthroplasty situations.

The acetabular implant shell is positioned into the acetabulum using the same acetabular shell impaction instrument used with the trial shell. Specifically, the distal connection end of the instrument is engaged and connected to the shell. The shell is partially inserted into the acetabulum until the rim begins to engage bone. The implant is then positioned with the instrument to the desired angular orientation, such as abduction and anteversion. Preferably, the shell is positioned with 20° to 25° of anteversion and with an abduction angle of about 35° to 45°. The anteversion can be verified using techniques known to those skilled in the art. The proximal impaction end of the instrument is then impacted with a mallet or similar instrument. Force from the mallet is transferred from the instrument to the shell as it is driven and permanently seated into the natural acetabulum. The shell should be driven into the acetabulum until the outer fixation spikes centrally engage into cancellous bone.

Providing a Driving Instrument (see FIGS. 5–7)

The driving instrument generally includes a working section and a driving section. The working section has a handle adapted to be gripped with a hand and manually rotated. The driving section has elongated drive shaft with a driving tip adapted to engage and hold a screw-hole plug or bone screw. A joint connector connects the working section to the driving section. This connector enables the two sections to move at various angles with respect to each other. Specifically, while the working section is positioned at an angle with respect to the driving section, the handle can be rotated to simultaneously rotate the driving tip. In this manner, screw-hole plugs and bone screws can be inserted through the small surgical incision and into the acetabular shell embedded in the natural acetabulum. The driving instrument is discussed in more detail with reference to FIGS. 5–7.

In one embodiment, a driving guide can be connected to the driving section of the driving instrument. The driving guide helps guide the driving section to the acetabular shell to insert an acetabular plug, screw-hole plug, dome plug, bone screw, or the like. The driving guide can be readily attached and removed from the driving section.

Figure 2:
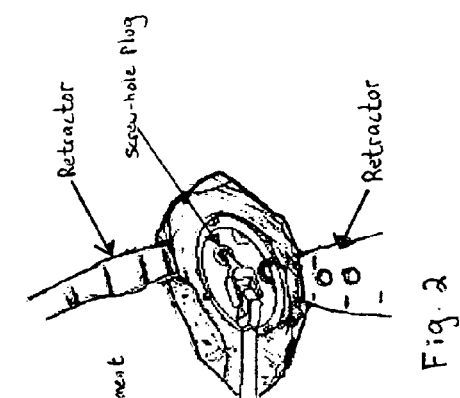
FIG. 2 is a view of an MIS incision with a driving instrument having a variably angled joint connector of the present invention inserting a screw-hole plug into an acetabular shell embedded in the acetabulum.
Figure 3:
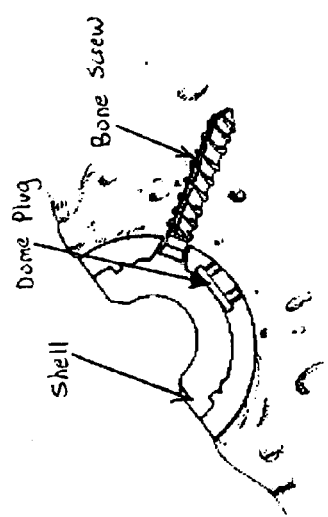
FIG. 3 is a view of an acetabular shell embedded in the acetabulum after a bone screw and dome plug have been placed with the driving instrument of the present invention.

Removing Screw-Hole Plugs (see FIGS. 2 and 3)

The implant shell may be provided with screw-hole plugs. In this instance, after the shell is properly seated in the acetabulum, one or more of the plugs may be removed with the driving instrument. This instrument is inserted through the incision, and the driving tip is engaged into the indentation of the plug. If the plugs are press-fit into the shell, then leverage is used to dislodge the screw-hole plug from the shell. If the plugs are screwed into the shell, then the handle is rotated to rotate the driving section and plug. The driving section and attached screw-hole plug are removed from the surgical site.

Installing Screw-Hole Plugs and a Dome Hole Plug (see FIGS. 2–3)

The implant shell may be provided with screw-hole plugs or a dome plug that may be installed or inserted into the shell. Typically, these plugs have a head with a tool engaging recess. A threaded shaft extends from the head and is adapted to threadably engage a threaded bore in the acetabular shell.

The driving tip of the driving section is engaged with the plug. Specifically, the driving tip frictionally engages with the tool engaging recess in the plug. The plug and driving section are then positioned into the surgical site so the threaded shaft on the plug engages the threaded bore in the acetabular shell. As the handle on the working shaft is rotated, the driving section simultaneously turns. The driving tip transfers torque to the plug and threads it into the threaded bore of the shell. Once the plug is fully threaded into the shell, the driving tip is disengaged from plug, and the driving section is removed from the surgical site. At this time, another plug can be attached to the driving tip and the process is repeated as needed. Further, the driving guide can be attached to the driving instrument to help guide and steer placement or removal of the plug.

Drilling Holes Through the Acetabular Shell for Bone Screws

Next, a drill bit is provided, connected to a flexible driver, and positioned into the selected screw hole at an angle up to about 16°. As the hole is drilled, care should be taken to protect the sciatic nerve and superior gluteal artery. A depth gauge may be inserted into the drilled holes to determine the depth for a corresponding bone screw. If desired, a tapping bit may be connected to the driver to tap the hole.

Installing Bone Screws Through the Acetabular Shell (see FIGS. 2–3)

A bone screw is inserted through the acetabular shell in a manner similar to inserting a screw-hole plug or dome plug. The driving tip of the driving section is engaged with the bone screw. Specifically, the driving tip frictionally engages with a tool engaging recess in the bone screw. This recess may be provided as a Phillip's type recess, hexagonal recess, or other recesses known in the art. The bone screw and driving section are then positioned into the surgical site so the threaded shaft on the bone screw passes through the screw-hole opening in the acetabular shell and into a drilled hole. As the handle on the working shaft is rotated, the driving section simultaneously turns. The driving tip transfers torque to the bone screw and drives it through the screw-hole opening and into adjacent cortical bone of the natural acetabulum. The bone screw should be seated into the countersunk holes of the shell so the acetabular insert can properly snap into the shell. Once the bone screw is fully threaded into the shell, the driving tip is disengaged from bone screw, and the driving section is removed from the surgical site. At this time, another bone screw can be attached to the driving tip and the process repeated as needed. Further, the driving guide can be attached to the driving instrument to help guide and steer placement or removal of the screws.

Figure 4:
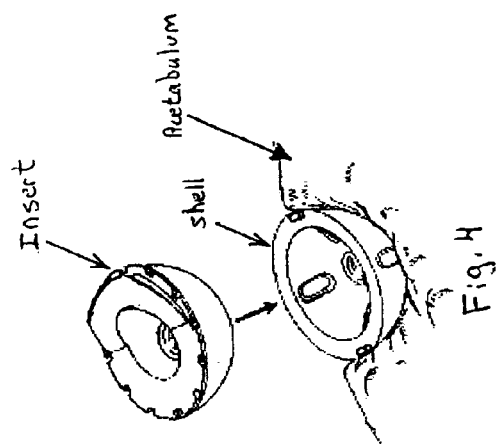
FIG. 4 is a view of an insert being inserted to an acetabular shell embedded in the acetabulum.

Inserting & Impacting Insert into Shell (see FIG. 4)

Various inserts known to those skilled in the art (such as standard, hooded, and protrusion inserts) can be inserted into the implant shell. Once the appropriate size and style insert is selected, the insert is connected to an instrument. The insert is positioned into the cavity of the shell and should be rotated to align with the antirotational pegs on the shell. A surgical mallet is used to strike the proximal end of the instrument to seat the insert into the shell.

Closing Surgical Site

Once the insert is firmly connected to the shell, all instruments and devices are removed from the site. The acetabular shell and insert should now be properly positioned. Closure of the site may occur with well known techniques, such as posterior and anterior lateral approaches. Further, this disclosure will not discuss post-operative protocol or rehabilitation as such procedures are known in the art and tailored to meet the specific needs of the patient.

DETAILED DESCRIPTION OF DRIVING INSTRUMENT

One important advantage of the present invention is that the instrument is specifically designed and adapted to be used in minimally invasive surgical techniques for aligning and driving screw-hole plugs, dome plugs, bone screws, and the like into a prosthetic acetabular shell that is embedded into the natural acetabulum of a patient.

FIGS. 5 and 6 show the driving instrument 10 of the present invention comprises two primary parts, a working section 12 and a driving section 14. Working section 12 has a proximal end 16 with a handle 18 that is adapted to be gripped with a hand. An elongated cylindrical working shaft 20 extends from the handle 18 and terminates at a distal end 24 having a working head 26.

Working head 26 is configured as an enlarged head with a U-shape. Two walls 30a and 30b extend oppositely from each other. A bar 32 extends between the walls and forms a recess or capture zone 34.

Driving section 14 has a proximal end 40 with a driving head 42. An elongated, cylindrical drive shaft 44 extends from the driving head and terminates at a distal end 46 having a driving tip 48. Driving head 42 is configured as an enlarged head with a U-shape. Two walls 50a and 50b extend oppositely from each other. A bar 52 extends between the walls and forms a recess or capture zone 54.

Driving head 42 has a complementary shape to working head 26. Together, these two heads interlock together and form a U-joint connector. Torque or rotating forces can be transmitted from the working head to the driving head even while the working section and driving section are disposed at an angle with respect to each other.

One important advantage of the present invention is that the working end can transmit forces to the driving tip while being at an angle relative to the driving section. This variability in angulation is particularly advantageous for performing minimally invasive hip replacement surgery for the acetabulum. In particular, the natural acetabulum is disposed at an angle with respect to the surgical incision. Traditional, straight driving instruments do not have the proper angle to properly engage the acetabular shell while it is embedded in the acetabulum. Since the driving section can be angled, the driving tip can squarely address and engage the screw-hole plugs, the dome plug, and screw-hole openings for inserting and removing bone screws.

Another important advantage of the present invention is that the driving section 14 is elongated with an extended driving shaft 44. Preferably, the driving section has a length of about 1 inch, but it may be between about 0.5 inches to about 1.5 inches. The length of this shaft is a critical element to the invention since it enables the driving instrument to reach deep into the surgical site and engage the acetabular shell.

The driving tip 48 may be formed with various configurations known to those skilled in the art. This tip, for example, may be formed as a star, polygon, Phillip's screwdriver connection, or other configuration adapted to engage and hold a bone screw, screw-hole plug, dome plug, or the like.

The handle may be formed from polymer, steel, or other suitable materials known in the art. Preferably, working shaft 20 and working head 26 are integrally formed together. Working shaft 20, working head 26, and driving section 14 are made from a strong, durable material, such as steel or other material suitable to transmit torque in a surgical application.

During placement of a bone screw, screw-hole plug, dome plug, or the like, the driving instrument can removeably connect with a driving guide 100, shown in FIG. 7. The guide 100 has an elongated handle 102 with a curved section or bend 104 at a distal end of the handle. This curve section leads to a connection end 106 formed as an enlarged cylindrical head with a bore 108. Bore 108 completely extends through the head and is sized to receive driving shaft 44 of driving section 14.

In use, the connection end 106 is slideably positioned over the driving shaft 44. A bone screw, screw-hole plug, dome plug, or the like is then attached to the driving tip 48. As the driving section 14 is positioned into the surgical site, the driving guide 100 can maneuver and guide the driving section 14. The driving guide, thus, can facilitate placement of the driving tip so the surgeon can easily, accurately, and quickly place and remove bone screws, screw-hole plugs, dome plugs, or the like to and from the acetabular shell.

One skilled in the art will appreciate that the joint connector formed from working head 26 and driving head 42 can have other configurations and still be within the scope of the invention. The U-joint connection is the preferred embodiment for this joint or connection between the working and handle sections, but other joints and connections would work too. For example, the joint connector could be formed with a ball and socket connection. The ball could be captured in the socket so rotation of the working section locks the ball and socket joint and simultaneously causes the driving section to rotate.

It should be emphasized that although the method of the present invention was described with a specific number and sequence of steps, these steps can be altered or omitted while other steps may be added without departing from the scope of the invention. As such, the specific steps discussed in the preferred embodiment of the present invention illustrate just one example of how to utilize the novel method and steps of the present invention. Further, although illustrative embodiments and methods have been shown and described, a wide range of modifications, changes, and substitutions is contemplated in the foregoing disclosure and in some instances, some features of the embodiments or steps of the method may be employed without a corresponding use of other features or steps. Accordingly, it is appropriate that the appended claims be construed broadly and in a manner consistent with the scope of the embodiments disclosed herein.

What is claimed is:

1. A method for using minimally invasive surgery to implant a prosthetic acetabular shell and insert into a natural acetabulum, comprising the steps of:

incising a hip with a minimally invasive incision;

implanting the acetabular shell into the natural acetabulum;

providing a driving instrument having a working section and a driving section connected together with a joint connector, wherein the working section includes a handle, the driving section includes a driving tip, and the joint connector enables the working section and driving section to move to various angles relative to each other;

attaching an acetabular plug to the driving tip of the driving section;

positioning the working section at an angle with respect to the driving section;

positioning the driving tip and acetabular plug through the incision to engage the acetabular shell;

rotating the handle to threadably engage the acetabular plug to the acetabular shell while the working section is at an angle relative to the driving section;

removing the driving instrument from the incision;

positioning the acetabular insert into the acetabular shell; and closing the incision.

2. The method of claim 1 wherein the step of incising a hip creates the minimally invasive incision with a length of about 2½ inches to about 4 to 5 inches.

3. The method of claim 2 further comprising the step of providing the joint connector as a U-joint.

4. The method of claim 1 further comprising the step of providing the driving section with a length of about one inch.

5. The method of claim 1 further comprising the step of positioning the working section at various angles with respect to the driving section while the acetabular plug is connected to the driving tip.

6. The method of claim 1 further comprising the steps of:

providing a driving guide;

connecting the driving guide to the driving section; and guiding the driving section with the driving guide while the driving tip and acetabular plug are positioned through the incision.

7. The method of claim 6 further comprising the step of removing the driving guide from the driving section after the step of removing the driving instrument from the incision.

8. The method of claim 1 further comprising the step of moving the driving section to various angles with respect to the working section.

9. A method for using minimally invasive surgery to implant a prosthetic acetabular shell into a natural acetabulum, comprising the steps of:

incising a hip with an incision with a length of between about 2.5 inches to about 5 inches;

implanting the acetabular shell into the natural acetabulum;

providing a driving instrument having a working section and a driving section connected together with a joint connector adapted to move the working section and driving section to various angles relative to each other;

attaching an acetabular bone screw to the driving section;

positioning the acetabular bone screw through the incision;

positioning the working section at an angle with respect to the driving section;

rotating the working section to drive the bone screw through the acetabular shell and into the natural acetabulum;

removing the driving instrument from the incision; and closing the incision.

10. The method of claim 9 further comprising the step of attaching a driving guide to the driving section of the driving instrument.

11. The method of claim 10 further comprising the step of guiding the bone screw and driving section with the driving guide to the acetabular shell.

12. The method of claim 11 further comprising the step of removing the driving guide from the driving section after the step of removing the driving instrument from the incision.

13. The method of claim 9 wherein the step of rotating the working section simultaneously rotates the driving section while the working section is angled with respect to the driving section.

14. The method of claim 13 further comprising the step of providing the driving section with a length of about one inch.

15. The method of claim 9 further comprising the steps of providing the driving section with a driving tip, and connecting the acetabular bone screw to the driving tip.

16. A method for implanting a prosthetic acetabular component into a natural acetabulum, comprising the steps of:

incising a hip with an incision;

implanting the acetabular component into the natural acetabulum;

providing a driving instrument having a working section and a driving section connected together with a joint connector adapted to move the working section and driving section to various angles relative to each other;

attaching to the driving section one of an acetabular bone screw, an acetabular screw-hole plug, and an acetabular dome plug;

positioning the driving section through the incision;

angling the working section with respect to the driving section;

rotating the working section to rotate the driving section to drive one of the acetabular bone screw, the acetabular screw-hole plug, and the acetabular dome plug;

removing the driving instrument from the incision; and closing the incision.

17. The method of claim 16 further comprising the step of providing the joint connector as a U-joint.

18. The method of claim 16 further comprising the step of providing the working section with a handle at a proximal end, and providing the driving section with a driving tip at a distal end.

19. The method of claim 18 further comprising the step of providing the driving section with an elongated, cylindrical drive shaft.

20. The method of claim 19 further comprising the step of providing the driving section with a length of between about 0.5 inches to about 1.5 inches.

* * * * *